(12) United States Patent
Angel et al.

(10) Patent No.: US 7,049,360 B2
(45) Date of Patent: May 23, 2006

(54) WATER-SOLUBLE OR WATER-DISPERSIBLE (CO) POLYMERS OF HYDROXYALKYL (METH) ACRYLATES, A PROCESS FOR THEIR PREPARATION, AND THEIR USE AS COATING AGENT, BINDER AND/OR FILM-FORMING EXCIPIENT PHARMACEUTICAL DOSAGE FORMS

(75) Inventors: Maximilian Angel, Schifferstadt (DE); Axel Sanner, Frankenthal (DE); Karl Kolter, Limburgerhof (DE)

(73) Assignee: BASF Aktienegesellschaft, Ludwigshafen (DE)

( * ) Notice: Subject to any disclaimer, the term of this patent is extended or adjusted under 35 U.S.C. 154(b) by 0 days.

(21) Appl. No.: 09/964,796

(22) Filed: Sep. 28, 2001

(65) Prior Publication Data
US 2002/0042466 A1 Apr. 11, 2002

(30) Foreign Application Priority Data
Oct. 4, 2000 (DE) ................ 100 49 297

(51) Int. Cl.
*C08K 3/20* (2006.01)
(52) U.S. Cl. ............... 524/459; 525/59; 526/202
(58) Field of Classification Search ........... 524/459, 524/503; 526/202; 424/482; 525/59
See application file for complete search history.

(56) References Cited

U.S. PATENT DOCUMENTS

| | | | | |
|---|---|---|---|---|
| 3,203,918 A | * | 8/1965 | Goldenberg et al. | 524/803 |
| 3,361,696 A | * | 1/1968 | Bolgiano et al. | 524/824 |
| 3,433,701 A | * | 3/1969 | Armour | 428/436 |
| 3,563,963 A | * | 2/1971 | Beier et al. | 526/93 |
| 3,669,691 A | * | 6/1972 | Long et al. | 426/102 |
| 3,817,896 A | * | 6/1974 | Bergmeister et al. | 524/817 |
| 4,397,968 A | | 8/1983 | Eck et al. | 523/305 |
| 4,581,394 A | | 4/1986 | Yoshida et al. | 524/557 |
| 5,354,803 A | * | 10/1994 | Dragner et al. | 524/503 |
| 6,107,397 A | | 8/2000 | Blankenburg et al. | 524/813 |

FOREIGN PATENT DOCUMENTS

| | | |
|---|---|---|
| DE | 31 11 602 | 10/1982 |
| DE | 196 29 948 | 1/1998 |
| DE | 197 12 247 | 10/1998 |
| GB | 1278813 | 6/1972 |
| WO | WO 92/07553 | 5/1992 |
| WO | WO 00/44356 | 8/2000 |

* cited by examiner

Primary Examiner—Bernard Lipman
(74) Attorney, Agent, or Firm—Novak Druce & Quigg LLP; Jason D. Voight

(57) ABSTRACT

The present invention relates to water-soluble or water-dispersible copolymers obtainable by free-radical polymerization of a) 80 to 20% by weight of hydroxy-$C_1$–$C_6$-alkyl (meth) acrylate and, where appropriate, one or more compounds of the formula (A) or (B)

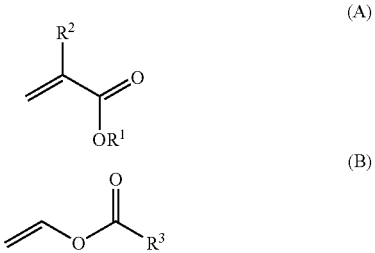

with $R^1$=H, $C_1$–$C_6$-alkyl,
$R^2$=H, $CH_3$
$R^3$=$C_1$–$C_{24}$-alkyl
or mixtures thereof
in the presence of b) 20 to 80% by weight of polyvinyl alcohol (PVA) and
c) where appropriate 0 to 20% by weight of other polymerizable compounds (C), a process for their preparation, and their use as coating agent, binder and/or film-forming excipient in pharmaceutical dosage forms.

12 Claims, No Drawings

WATER-SOLUBLE OR WATER-DISPERSIBLE (CO) POLYMERS OF HYDROXYALKYL (METH) ACRYLATES, A PROCESS FOR THEIR PREPARATION, AND THEIR USE AS COATING AGENT, BINDER AND/OR FILM-FORMING EXCIPIENT PHARMACEUTICAL DOSAGE FORMS

The present invention relates to water-soluble or water-dispersible copolymers of hydroxyalkyl (meth)acrylates, a process for their preparation, and their use as coating agent, binder and/or film-forming excipient in pharmaceutical dosage forms.

Solid pharmaceutical dosage forms such as tablets, capsules, pellets, granules, crystals etc. are coated, i.e. provided with a film coating, for a wide variety of reasons. It is possible in this way, for example, to mask an unpleasant odor or taste, and improve the swallowability. The stability of the active ingredient can be increased by the coating, since less water vapor and oxygen reaches the interior of the tablets. The dosage forms have a better appearance and can be distinguished better by incorporating dyes. In addition, in particular the rate of release of the active ingredient can be adjusted by the film coating.

A distinction is made in general between instant release forms and sustained or slow release forms.

In the case of instant release forms, the disintegration of the tablet and the release of the active ingredient from the dosage form should, where possible, be unaffected by the coating, for which reason the film coating must dissolve rapidly in gastric fluid. In addition, it must have good film properties. The tensile strength and the ultimate elongation ought to be high so that the film coating withstands mechanical effects like those occurring during pharmaceutical processing—especially packaging—and during transport and storage.

A product which is frequently employed for coating instant release tablets is hydroxypropylmethylcellulose (HPMC). Hydroxypropylmethylcellulose shows a steep rise in viscosity with increasing concentration in aqueous solution. Hydroxypropylcellulose (HPC) also shows a similar behavior.

Since the film former solution must be finely atomized for coating tablets, and the drops which are formed must thoroughly wet the surface of the tablets, and moreover spread well, the viscosity must not exceed a certain limit (between 150 and 250 mPas), which depends on the type of spray nozzle and the equipment. It is therefore possible in the case of HPMC to employ only relatively low film former concentrations.

The recommendation given in the literature for the concentration of Pharmacoat® 606 (from Shin-etsu) is 5 to 7% by weight (Pharmaceutical Coating Technology, edited by Graham Cole, Taylor and Francis Ltd. 1995 and manufacturers' technical data sheets). These low spray concentrations result in a relatively long processing time and thus high costs.

In addition, hydroxypropylmethylcellulose has other disadvantages, inter alia in the wetting characteristics, in the adhesiveness on the tablet surface, in the pigment binding capacity, in the mechanical properties of the films, in the hygroscopicity and in the permeability for water vapor and oxygen, in the rate of solution and in the difference in disintegration time between film-coated tablet and core.

The low elasticity of the films of hydroxypropylmethylcellulose frequently lead to the film-coated tablets splitting open on storage in moist conditions, as a consequence of the swelling of the core. Even the use of plasticizers results in negligible improvements in this problem. On the contrary, it may lead to tacky films and, through migration, to changes in the tablet properties.

Binders are employed in pharmaceutical dosage forms in order to increase the processability and the mechanical strength. They are normally employed in tablets, granules and pellets and result in improved flowability, greater hardness and less friability.

The binders used at present such as maltodextrin or polyvinylpyrrolidone frequently do not result in satisfactory hardnesses and friabilities. Other binders such as starch paste and hydroxypropylmethylcellulose (HPMC) can be employed only in low concentrations because of their high viscosity.

In addition, film-forming excipients are employed in solutions and sprays which are applied to the skin or mucous membrane or else introduced systemically into the body. Examples thereof are reparations for wound treatment and spray-on dressings, but also reparations for application to intact skin or mucous membrane. In this case, the skin is protected by a film, and the active ingredients can penetrate into or through the skin.

Great flexibility is necessary for transdermal therapeutic systems and for wound plasters, just as for the abovementioned dosage forms, but the products available at present do not have this. The use of possible plasticizers to achieve the necessary flexibility is undesirable for toxicological and pharmacological reasons.

GB 1 278 813 describes acrylate emulsion polymers which are distinguished by high water resistance compared with conventional soap dispersions, which makes them unsuitable for use in instant release tablets.

DE 31 11 602 describes emulsion polymers which are stabilized by polyvinyl alcohol and comprise at least 60% by weight (meth)acrylate and/or styrene units. They are used as binders for emulsion paints and adhesives.

DE-A 196 29 948 discloses dispersions in which styrene is an obligatory constituent and which are used as starting materials in building materials.

It is an object of the present invention to provide water-soluble or water-dispersible polymers as coating agents, binders and/or film-forming excipients in pharmaceutical dosage forms, in particular for instant release forms, which do not have the abovementioned disadvantages.

We have found that this object is achieved by water-soluble or water-dispersible copolymers which are obtainable by free-radical polymerization, preferably emulsion polymerization, of a) 80 to 20% by weight of hydroxy-$C_1$–$C_6$-alkyl (meth) acrylate and, where appropriate, one or more compounds of the formula (A) or (B)

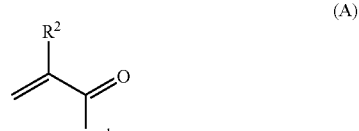

(A)

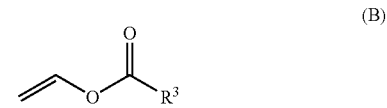

(B)

with $R^1$=H, $C_1$–$C_6$-alkyl, $R^2$=H, $CH_3$
$R^3$=$C_1$–$C_{24}$-alkyl
or mixtures thereof in the presence of
b) 20 to 80% by weight of polyvinyl alcohol (PVA) and
c) where appropriate 0 to 20% by weight of other polymerizable compounds (C).

The invention further relates to a process for preparing the copolymers by free-radical polymerization, preferably emulsion polymerization, in an aqueous or nonaqueous but water-miscible solvent or in mixed nonaqueous/aqueous solvents. Preparation in water as solvent or dispersant is preferred.

Examples of suitable nonaqueous solvents are alcohols such as methanol, ethanol, n-propanol and isopropanol, and glycols such as ethylene glycol and glycerol.

The hydroxy-$C_1$–$C_6$-alkyl (meth)acrylate preferably employed is hydroxymethyl methacrylate, hydroxyethyl methacrylate, hydroxypropyl methacrylate, hydroxybutyl methacrylate or hydroxypentyl methacrylate, particularly preferably hydroxyethyl methacrylate. The compounds of the formula (A) which are preferably employed are $C_1$–$C_6$-alkyl (meth)acrylates, in particular methyl methacrylate, ethyl acrylate and methyl acrylate or mixtures thereof. The compounds of the formula B employed are $C_3$–$C_{24}$ vinyl esters, in particular vinyl acetate. Compounds of the formula A are preferred to compounds of the formula (B).

Suitable and preferred compounds (C) are: acrylic and methacrylic acids. Further compounds (C) are crotonic acid, mono($C_1$–$C_8$)-alkyl maleates, maleic acid, fumaric acid, itaconic acid, (meth) acrylonitrile, ethylenically unsaturated di ($C_1$–$C_{22}$)-alkyl dicarboxylates, preferably butyl maleate, ethylenically unsaturated sulfonic acids or sulfonic acid derivatives such as vinylsulfonic acid or the alkali metal salts thereof, acyclic N-vinylcarboxamides and N-vinyllactams such as vinylpyrrolidone.

It is also possible for multiply ethylenically unsaturated copolymerizable compounds which can act as crosslinkers to be present, preferably from the group of divinylbenzene, diallyl phthalate, butanediol diacrylate, butanediol dimethacrylate. Further suitable crosslinking monomers are mentioned, for example, in DE 197 12 247 A1, page 5. However, the content of compounds (C) is preferably 0% by weight.

A preferred embodiment of the invention comprises water-soluble or water-dispersible copolymers which are obtainable by free-radical polymerization, preferably emulsion polymerization, of
a) 80 to 20% by weight of hydroxy-$C_1$–$C_6$-alkyl (meth) acrylate and, where appropriate, one or more compounds of the formula (A) or (B)

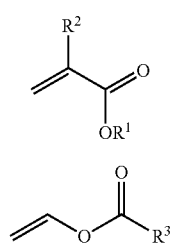

with $R^1$=H, $C_1$–$C_6$-alkyl,
$R^2$=H, $CH_3$ $R^3$=$C_1$–$C_{24}$-alkyl
or mixtures thereof in the presence of
b) 20 to 80% by weight of polyvinyl alcohol (PVA) and
c) where appropriate 0 to 20% by weight of other polymerizable compounds (C), where the content of hydroxy-$C_1$–$C_6$-alkyl (meth)acrylate in % by weight is at least once, preferably twice, in particular three times, as large as the content of compounds of the formula (A) or (B) in % by weight.

Suitable and preferred polyvinyl alcohols (PVA) are partially hydrolyzed, as well as completely hydrolyzed, (cold) water-soluble FVA with molecular weights between about 2000 and about 250,000, in particular about 10,000 to 100,000, as are obtained by alcoholysis or hydrolysis of polyvinyl esters, preferably of polyvinyl acetates. Preferred PVA have a degree of hydrolysis of from 65 to 99%, particularly preferably of from 80 to 90%.

The polymerization preferably takes place in the presence of from 20 to 80% by weight, preferably of from 25 to 60% by weight, in particular of from 30 to 55% by weight, of polyvinyl alcohol. The "remainder" up to 100% by weight is in each case constituted by the compounds hydroxy-$C_1$–$C_6$-alkyl (meth)acrylate, A and/or B or (C).

If one or more compounds of the formula A or B are employed in addition to hydroxy-$C_1$–$C_6$-alkyl (meth)acrylates, the content of hydroxy-$C_1$–$C_6$-alkyl (meth)acrylates in % by weight is at least once, preferably at least twice, particularly preferably at least three times, as large as the content of compounds of the formula (A) or (B) in % by weight.

The polymers can be prepared by polymerizing the monomers of the formula A and/or B and/or C in the presence of the PVA both with the aid of free-radical initiators and by the action of high-energy radiation, which is intended to be understood to include the action of high-energy electrons.

The emulsion polymerization is preferably carried out at temperatures of from 60 to 100° C.

The emulsion polymerization is initiated by employing free-radical initiators. The amounts of initiator or initiator mixtures used are between 0.01 and 10% by weight, preferably between 0.3 and 5% by weight, based on monomer employed.

Depending on the nature of the solvent used, both organic and inorganic peroxides or azo initiators are suitable, such as azobisisobutyronitrile, azobis (2-amidinopropane) dihydrochloride or 2,2'-azobis(2-methylbutyronitrile).

Examples of peroxide initiators are dibenzoyl peroxide, diacetyl peroxide, succinyl peroxide, tert-butyl perpivalate, tert-butyl per-2-ethylhexanoate, tert-butyl permaleate, bis (tert-butylperoxy)cyclohexane, tert-butylperoxy isopropyl carbonate, tert-butyl peracetate, 2,2-bis(tert-butylperoxy)butane, dicumyl peroxide, di-tert-amyl peroxide, di-tert-butyl peroxide, p-menthane hydroperoxide, pinane hydroperoxide, cumene hydroperoxide, tert-butyl hydroperoxide, hydrogen peroxide and mixtures of said initiators. Said initiators can also be used in combination with redox components such as ascorbic acid.

Alkali metal or ammonium persulfates are particularly suitable as initiator.

The free-radical emulsion polymerization preferably takes place in water in the presence of polyvinyl alcohol and in the presence of free-radical polymerization initiators, where appropriate emulsifiers, where appropriate other protective colloids, where appropriate molecular weight regulators, where appropriate buffer systems, and where appropriate subsequent pH adjustment using bases or acids. The copolymers are obtained as aqueous dispersions or aqueous solutions with a viscosity of less than 500 mPas, preferably less than 250 mPas, particularly preferably less than 150 mPas, or, after removal of the water content, as water-dispersible or water-soluble powders.

Suitable protective colloids besides PVA are water-soluble cellulose derivatives, preferably from the group of hydroxyethylcellulose, carboxymethylcellulose, carboxymethylhydroxyethylcellulose, methylhydroxyethylcellulose, or water-soluble (co)polymers composed of N-vinylamide compounds of N-vinyllactam compounds, preferably polyvinylpyrrolidone (PVP), or water-soluble polymeric, copolymeric or block-copolymeric polyalkylene oxides, preferably of ethylene oxide and/or propylene oxide.

Suitable molecular weight regulators are hydrosulfide compounds such as alkyl mercaptans, e.g. n-dodecyl mercaptan, tert-dodecyl mercaptan, thioglycolic acid and its esters, mercaptoalkanols such as mercaptoethanol. Other suitable regulators are mentioned, for example, in DE 197 12 247 A1, page 4. The amount required of the molecular weight regulators is in the range from 0 to 5% by weight based on the amount of (co)monomers to be polymerized, in particular 0.05 to 2% by weight, particularly preferably 0.1 to 1.5% by weight.

Examples of emulsifiers used are ionic or nonionic surfactants, whose HLB is normally in the range from 3 to 13. Concerning the definition of the HLB, reference is made to the publication by W. C. Griffin, J. Soc. Cosmetic Chem., Volume 5, 249 (1954).

The type of emulsifier and the mode of addition of the emulsifier influence the polymerization: it is possible in this connection to observe differences in the particle size, particle size distribution, stability of the copolymer dispersion and the extent of the grafting reactions, for example depending on whether the emulsifier is present in the initial charge or is metered in during the copolymerization. Examples of preferred anionic emulsifiers for preparing anionic emulsion copolymers are surface-active alkyl sulfates, alkylsulfonates, alkylaryl sulfates, alkylarylsulfonates, alkali metal and/or ammonium salts of alkyl or alkylaryl monoglycol or polyglycol ether sulfates. Preferred nonionic emulsifiers are, for example, ethoxylated fatty alcohols or ethoxylated alkylphenols. Particularly preferably used according to the invention is sodium lauryl sulfate, also in combination with polysorbate 80.

The amount of surfactants is 0.05 to 10% by weight, preferably 0.1 to 5% by weight, based on the polymer.

In the case of emulsion polymerization, it may be of crucial importance whether the monomer is metered in as such or as an aqueous emulsion. The aqueous emulsion of the monomers usually contains water, anionic and/or nonionic emulsifiers and/or protective colloids such as polyvinyl alcohol and, where appropriate, other protective colloids and, where appropriate, regulators The monomer or a monomer mixture or the monomer emulsion is introduced together with the initiator, which is generally present in solution, into a stirred reactor at the polymerization temperature (batch process) or, where appropriate, metered continuously or in a plurality of consecutive stages into the polymerization reactor (feed process). It is usual in the feed process for the reactor to be charged before starting the actual polymerization with, besides water (in order to make stirring of the reactor possible), also partial quantities, rarely the entire amount intended for the polymerization, of the starting materials such as emulsifiers, protective colloids, monomers, regulators etc. or partial quantities of the feeds (generally monomer feed or emulsion feed and initiator feed).

It must also be taken into account that copolymerization of each of the comonomers used must be possible in principle and that it also in fact takes place. In the simplest case, this can be estimated with the assistance of the copolymerization parameters or the Q and e values (cf., for example, B. Brandrup, Immergut, Polymer Handbook, $2^{nd}$ ed. (1975), John Wiley & Sons, New York).

It is thus possible where appropriate for a copolymerization in some circumstances to be made feasible by having one or more monomer components present in the initial charge and metering in the remaining monomer or the remaining monomer mixture only during the polymerization.

The solids content of the resulting aqueous polymer dispersions or solutions is usually 10 to 70% by weight, preferably 20 to 60% by weight, particularly preferably 25 to 40% by weight.

The polymer dispersions or solutions can be converted into powder form by various drying processes such as, for example, spray drying, fluidized spray drying, drum drying or freeze drying. Spray drying is preferably employed as drying process owing to the advantageously low viscosity of the polymer solutions or dispersions. An aqueous dispersion or solution can be prepared anew from the resulting dry polymer powder by redispersion in water. Conversion into powder form has the advantage that storability is improved, transportability is simpler and the tendency to be attacked by microbes is reduced.

The water-soluble or water-dispersible copolymers of the invention are outstandingly suitable as dispersible film former, binder, wetting aid and/or solubilizer for pharmaceutical dosage forms.

The flexibility and low viscosity mean that no additional plasticizers are usually necessary.

The invention therefore also relates to pharmaceutical dosage forms comprising at least one water-soluble or water-dispersible polymer of the invention as coating agent, binder and/or film-forming excipient.

The coated dosage forms are preferably, inter alia, film-coated tablets, film-coated microtablets, sugar-coated tablets, coated pastilles, capsules, crystals, granules or pellets.

The dosage forms containing binders are preferably, inter alia, tablets, microtablets, cores, granules or pellets.

The polymers of the invention can also be used to produce solutions and sprays which form a film on application to the skin or mucous membrane. The great elasticity and adhesiveness mean that the films adhere to the skin or mucous membrane for a long time. The frequency of application can thus be reduced, and the comfort of wearing is increased. Examples thereof are spray-on dressings for wounds, disinfectant sprays, solutions with mycostatics, sprays or solutions for the mouth with antibiotics etc. The flexibility also means that use in transdermal therapeutic systems is advantageous.

The copolymers used according to the invention easily wet lipophilic surfaces and have excellent protective colloid properties. Incorporated into suspensions and emulsions, they attach themselves to the particles of the disperse phase and stabilize it. They can therefore be used as wetting aids and stabilizers in disperse systems.

They improve the solubility and rate of dissolution of medicinal substances of low solubility in water by interacting with them, whereby the absorbability and bioavailability of the medicinal substances are improved. This advantageous effect is evident, for example, with dosage forms in which the active ingredient is not present in solution, such as, for example, tablets, granules, suspensions etc.

The polymers used according to the invention can, where appropriate also in combination with other excipients, be processed together with active ingredients to give polymer/active ingredient melts which either undergo extrusion and calendering to give drug products or, after the extrusion, are converted into granules or powders and only then processed to drug forms, for example compressed to tablets. In these cases, the copolymers introduce the properties detailed above into the dosage form.

The polymers of the invention are able to perform the following functions outstandingly in various pharmaceutical dosage forms:

Dispersing aid, suspending aid, wetting agent, solubilizer for medicinal substances of low solubility, emulsifier, crystallization inhibitor, anticaking aid, protective colloid, spreading aid, viscosity regulator, excipient for producing solid solutions with medicinal substances, excipient for adjusting release of active ingredient.

When used to produced suppositories and pessaries, the polymers on the one hand ensure the flexibility of the dosage form, and on the other hand promote the disintegration and the dissolution of active ingredient, and they coat the mucous membrane with an active ingredient-containing film which enhances absorption. As the comparison of the viscosities of the polymers of the invention (Example 1, viscosity 77 mPas) with corresponding solutions of hydroxymethylpropylcellulose (Pharmacoat 606) (Example 1, viscosity 2000 mPas) shows, the polymers of the invention have a considerably lower viscosity.

It is thus possible to employ more concentrated polymer preparations when coating tablets with the polymer dispersions, as well as for binder applications, which allows the processes to be made considerably more cost-effective and time-saving.

The dissolution or redispersion of the polymers in powder or granule form to give aqueous dispersions or solutions takes place considerably more quickly than with other film formers or binders, because the polymers of the invention are thoroughly wetted by water and show little agglomeration and a very high dissolution rate.

Gastric fluid-soluble tablets coated with the polymers show a disintegration time which is only slightly longer than that for the core, i.e. the film coating dissolves very rapidly in simulated gastric fluid.

In addition, the mechanical strength of the tablets is increased very much more when the polymers are used according to the invention than with hydroxypropylmethylcellulose.

Tablets swell to different extents depending on the excipients and active ingredients used, the storage time and the storage conditions, such as temperature and humidity. A rigid film coating develops cracks when the core swells. The elasticity of film formers is therefore an important quantity. The copolymers of the invention have an exceptionally high flexibility and elasticity. Thus, the ultimate elongation may be up to 300%. No crack formation is therefore to be expected, even if the core swells greatly.

The polymers can be applied in pure form or else together with conventional excipients to the active ingredient-containing core. Examples of conventional excipients are colored pigments for coloring, white pigments such as titanium dioxide to increase the hiding power, talc and silica as non-stick agents, polyethylene glycols, glycerol, propylene glycol, triacetin, triethyl citrate as plasticizer and various surface-active substances such as sodium lauryl sulfate, polysorbate 80, Pluronics und Cremophors to improve the wetting characteristics. The substances mentioned by way of example do not represent a restriction. It is possible to use all additives known to be suitable for gastric fluid-soluble film coatings.

It is also possible to combine the polymers used according to the invention with other film formers or polymers in the ratio from 1:9 to 9:1.

Examples of polymers which can be employed for this purpose are the following:

Polyvinylpyrrolidone, polyvinylpyrrolidone copolymers, water-soluble cellulose derivatives such as hydroxypropylcellulose, hydroxypropylmethylcellulose, methylcellulose, hydroxyethylcellulose, acrylate and methacrylate copolymers, polyvinyl alcohols, polyethylene glycols, polyethylene oxide/polypropylene oxide block copolymers.

The coating processes which can be used are the conventional processes such as coating in a fluidized bed or in a horizontal drum coater, the drip-coating process and the pan-coating process. Besides the use for tablets, the polymers of the invention can also be employed for coating other pharmaceutical preparations such as granules, pellets, crystals or capsules. The novel coating agents are applied in a conventional manner in a thickness of from 5 to 200 µm, preferably 10 to 100 µm.

In their use as binder, a distinction is made between wet and dry binders depending on the processing method. The latter are used inter alia for direct tabletting and for dry granulation or compaction. In these cases, the binder is mixed with the active ingredient and, where appropriate, other excipients and then directly tabletted, or granulated or compacted.

In contrast thereto, in wet granulation the active ingredient/excipient mixture is moistened with a solution of the binder in water or an organic solvent, and the moist composition is passed through a sieve and then dried. The moistening and drying may moreover take place in parallel, such as, for example, in fluidized-bed granulation.

For optimal processing, the binder should have low viscosity in solution because viscous solutions lead to inhomogeneous granules.

A binder should lead to uniform, hard, nonfriable granules or tablets. The hardness is particularly important for tablets because many active ingredients are difficult to compress and thus afford tablets with inadequate mechanical stability.

In addition, the binder should have a negligible adverse effect on the disintegration of the drug forms and the rate of release of the active ingredients.

The most commonly used binders are, for example, polyvinylpyrrolidone, vinyl acetate/vinylpyrrolidone copolymers, gelatin, starch pastes, maltodextrins, hydroxyalkylated and carboxyalkylated cellulose derivatives, such as hydroxypropylmethylcellulose, methylcellulose, sodium carboxymethylcellulose, natural gum types such as gum arabic, pectin or alginate.

Many of these binders have a high viscosity in solution and are difficult to process. The high viscosity means that the powder particles to be granulated are poorly and nonuniformly wetted, resulting in a granule strength which is too low and a particle size distribution which is unfavorable.

Many binders are moreover hygroscopic and swell on absorption of water. This may drastically alter the properties of granules and tablets.

It has now been found, surprisingly, that the polymers of the invention have excellent effects as binders and, moreover, have a negligible effect on disintegration in concentration ranges from 0.5 to 20% by weight, preferably 1 to 10% by weight, of the total amount of the formulation. Because the copolymers have good wetting characteristics, it is moreover possible to improve the release of active ingredients of low solubility.

When the copolymers are used as binders the resulting granules or tablets are exceptionally mechanically stable and also stable on storage for long periods.

The preparation and use of the copolymers of the invention is explained in detail in the following examples without, however, restricting the invention to the exemplary embodiments.

EXAMPLE 1

| Composition | 35% by weight | Mowiol 4-88 (polyvinyl alcohol, from Clariant) |
| --- | --- | --- |
| | 55% by weight | hydroxyethyl methacrylate |
| | 10% by weight | methyl methacrylate |
| Precharge | 230.0 g | of deionized water |
| | 0.7 g | of sodium lauryl sulfate |
| | 101.5 g | of Mowiol ® 4-88 |
| | 30 ml | of feed 1 |
| Feed 1 | 550.0 g | of deionized water |
| | 0.3 g | of sodium lauryl sulfate |
| | 133.3 g | of Mowiol ® 4-88 as 30% strength aqueous solution |
| | 220.0 g | of hydroxyethyl methacrylate |
| | 40.0 g | of methyl methacrylate |
| Feed 2 | 5.0 g | of 7% strength aqueous sodium persulfate solution |
| Feed 3 | 30.0 g | of 7% strength aqueous sodium persulfate solution |
| | 55.0 g | of deionized water |

Apparatus: 2 l pilot stirred apparatus, oil bath, anchor stirrer, process control system for feeds The apparatus is flushed with nitrogen Procedure The precharge was heated to an internal temperature of 80° C. At about 75° C., feed 2 was metered in and polymerized for 15 minutes. Feed 1 was added in 1.5 h, and feed 3 was added simultaneously in 10 minutes. Polymerization was continued at 80° C. for 3 h after completion of feed 1. The mixture was then cooled and filtered through 120 mm.

| Solids content | 28.9% by weight |
| --- | --- |
| Average particle size | 325 nm |
| Coagulum | 0.1 g |
| Viscosity (20% solution) | 77 mPas |
| Film properties (54% R.H., 23° C.) | |
| | |
| Ultimate elongation | 43% |
| Tear strength | 45 N/mm² |
| Comparison Pharmacoat ® 606 (from Shin-etsu) | |
| | |
| Viscosity (20% solution) | 2000 mPas |
| Film properties (54% R.H., 23° C.) | |
| | |
| Ultimate elongation | 17% |
| Tear strength | 58 N/mm² |

Use Example

Production of propranolol HCl film-coated tablets (gastric fluid-soluble coating)

A film coating of the following composition:

| Polymer from Example 1 | 12.0% by weight |
| --- | --- |
| Polyvinyl alcohol/hydroxyethyl methacrylate/methyl methacrylate | weight |
| Sicovit ® rot (from BASF Aktiengesellschaft) | 1.5% by weight |
| Titanium dioxide BN 56 (from Kronos) | 3.0% by weight |
| Talcum powder (from Riedel de Haen) | 4.5% by weight |
| Water | 79.0% by weight | was sprayed onto 9 mm biconvex tablet cores containing 40 mg of propranolol HCl (from Knoll AG), 195.0 mg of Ludipress® (from BASF Aktiengesellschaft), 12.50 mg of Kollidon® VA 64 (from BASF Aktiengesellschaft) and 2.50 mg of magnesium stearate in a horizontal drum coater (Accela-Cota 24", from Manesty).

The spray dispersion was prepared by redispersing the spray-dried polymer from Example 1 in water by stirring, adding Sicovit® rot, titanium dioxide and talcum and then homogenizing in a corundum disk mill. 1090 g (including an overage of 10% for spray losses) were applied to 5000 g of cores at an inlet air temperature of 55° C. and a spraying rate of 31 g/min using a spraying nozzle with a width of 1.0 mm and a spraying pressure of 1.8 bar. The spraying was followed by drying at 55° C. for 5 min.

Smooth, glossy, red film-coated tablets were obtained with the following properties:

| Appearance: | very smooth surface, nicely formed imprint |
| --- | --- |
| Disintegration (simulated gastric fluid): | 5 min. 13 s. |
| Disintegration time difference (coated tablet-core): | 55 s. |
| Hardness: | 94 N |
| Hardness difference (Coated tablet-core): | 24 N |

We claim:

1. A water-soluble or water-dispersible copolymer obtained by free-radical polymerization of a monomer mixture consisting essentially of
   a) 80 to 20% by weight of a mixture of hydroxy-$C_1$–$C_6$-alkyl(meth)acrylate and one or more compounds of the formula (A) or (B)

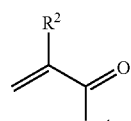
(A)

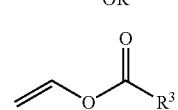
(B)

with $R^1$=H, $C_1$–$C_6$-alkyl,
$R^2$=H, $CH_3$,
$R^3$=$C_1$–$C_{24}$-alkyl,
or mixtures thereof, wherein the content of the content of hydroxy-$C_1$–$C_6$-alkyl(meth)acrylate in % by weight in a) is at least equal to the one or more compounds of the formula (A) or (B) in % by weight,
in the presence of,
b) 20 to 80% by weight of polyvinyl alcohol (PVA) and
c) 0 to 20% by weight of other polymerizable compounds (C) selected from the group consisting of acrylic and methacrylic acids, crotonic acid, mono($C_1$–$C_8$)-alkyl maleates, maleic acid, fumaric acid, itaconic acid, (meth)acrylonitrile, ethylenically unsaturated di($C_1$–$C_{22}$)-alkyl dicarboxylates, ethylenically unsaturated sulfonic acids or sulfonic acid derivatives, acyclic N-vinylcarboxamides and N-vinyllactams.

2. A water-soluble or water-dispersible copolymer as claimed in claim 1, wherein the free-radical polymerization is an emulsion polymerization.

3. A water-soluble or water-dispersible copolymer as claimed in claim 1, wherein the hydroxyethyl methacrylate is employed as hydroxy-$C_1$–$C_6$-alkyl (meth)acrylate.

4. A water-soluble or water-dispersible copolymer as claimed in claim 1, wherein the compounds of the formula (A) are selected from the group consisting of methyl methacrylate, ethyl acrylate, methyl acrylate, and mixtures thereof.

5. A water-soluble or water-dispersible copolymer as claimed in claim 1, wherein the compounds of the formula (B) are selected from the group consisting of $C_3$–$C_{24}$-vinyl esters.

6. A process for preparing water-soluble or water-dispersible copolymers as claimed in claim 1 by free-radical polymerization in an aqueous or nonaqueous but water-miscible solvent or in mixed nonaqueous/aqueous solvents.

7. A process as claimed in claim 6, wherein the polymerization takes place in the presence of from 30 to 55% by weight of polyvinyl alcohol.

8. A pharmaceutical dosage form comprising at least one water-soluble water-dispersible copolymer as claimed in claim 1 as coating agent, binder and/or film-forming excipient.

9. A method for delivering a pharmaceutically active ingredient to a patient, said method comprising orally administering to the patient the pharmaceutical dosage form of claim 8.

10. A water-soluble or water-dispersible copolymer as claimed in claim 1, wherein the content of the content of hydroxy-$C_1$–$C_6$-alkyl(meth)acrylate in % by weight in a) is at least twice as much as the content of the one or more compounds of the formula (A) or (B) in % by weight.

11. A water-soluble or water-dispersible copolymer as claimed in claim 1, wherein the content of the content of hydroxy-$C_1$–$C_6$-alkyl(meth)acrylate in % by weight in a) is at least three times as much as the content of the one or more compounds of the formula (A) or (B) in % by weight.

12. A water-soluble or water-dispersible copolymer obtained by free-radical polymerization of a monomer mixture consisting of
a) 75 to 20% by weight of a mixture of hydroxy-$C_1$–$C_6$-alkyl(meth)acrylate and one or more compounds of the formula (A) or (B)

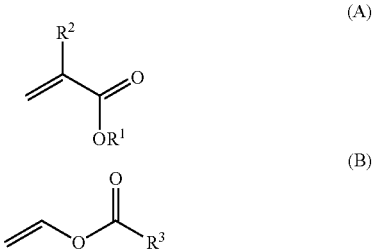

with $R^1$=H, $C_1$–$C_6$-alkyl,
$R^2$=H, $CH_3$,
$R^3$=$C_1$–$C_{24}$-alkyl,
or mixtures thereof,
wherein the content of the content of hydroxy-$C_1$–$C_6$-alkyl(meth)acrylate in % by weight in a) is at least equal to the one or more compounds of the formula (A) or (B) in % by weight,
in the presence of,
b) 25 to 60% by weight of polyvinyl alcohol (PVA) and
c) 0 to 20% by weight of other polymerizable compounds (C) selected from the group consisting of acrylic and methacrylic acids, crotonic acid, mono($C_1$–$C_8$)-alkyl maleates, maleic acid, fumaric acid, itaconic acid, (meth)acrylonitrile, ethylenically unsaturated di($C_1$–$C_{22}$)-alkyl dicarboxylates, ethylenically unsaturated sulfonic acids or sulfonic acid derivatives, acyclic N-vinylcarboxamides and N-vinyllactams.

* * * * *